(12) United States Patent
Sanuki et al.

(10) Patent No.: US 8,529,547 B2
(45) Date of Patent: Sep. 10, 2013

(54) METHOD OF COLLECTING SPECIMEN AND METHOD OF DIAGNOSING SUBJECT TO DETECT UPPER DIGESTIVE SYSTEM DISEASE

(75) Inventors: Hiromi Sanuki, Yokohama (JP); Nao Moriya, Hachioji (JP); Rie Kataoka, Fuchu (JP); Tetsuhide Takeyama, Hachioji (JP); Kyoko Yamamoto, Hachioji (JP)

(73) Assignees: Olympus Corporation, Tokyo (JP); Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/438,866

(22) Filed: Apr. 4, 2012

(65) Prior Publication Data
US 2012/0258478 A1    Oct. 11, 2012

Related U.S. Application Data

(60) Provisional application No. 61/471,868, filed on Apr. 5, 2011.

(51) Int. Cl.
*A61M 1/00* (2006.01)
*G01N 33/00* (2006.01)

(52) U.S. Cl.
USPC .......................................... 604/540; 604/319

(58) Field of Classification Search
None
See application file for complete search history.

(56) References Cited

U.S. PATENT DOCUMENTS

| 5,651,769 | A | 7/1997 | Waxman et al. | |
|---|---|---|---|---|
| 6,498,143 | B1* | 12/2002 | Beck et al. | 514/9.7 |
| 2002/0135766 | A1* | 9/2002 | Darrow et al. | 356/364 |
| 2007/0015156 | A1* | 1/2007 | Goggins | 435/6 |
| 2007/0213631 | A1* | 9/2007 | Kondo et al. | 600/562 |

OTHER PUBLICATIONS

Molner, I.G. et al., "CEA levels in fluids bathing gastrointestinal tumors", Gastroenterology (1976) 70(4):513-515.*
Osnes, M., "Studies on recovery and variation of pancreatic juice obtained by endoscopic cannulation of the main pancreatic duct in man", Scandinavian Journal of Gastroenterology (1981) 16(1):39-44 (abstract only).*
Noh, et al., "Do Cytokine Concentrations in Pancreatic Juice Predict the Presence of Pancreatic Diseases?"; Clinical Gastroenterology and Hepatology; Jun. 2006, pp. 782-789, vol. 4. No. 6.

* cited by examiner

*Primary Examiner* — Shafiqul Haq
*Assistant Examiner* — Gary E Hollinden
(74) *Attorney, Agent, or Firm* — Scully, Scott, Murphy & Presser, P.C.

(57) ABSTRACT

A method of collecting a specimen of the present invention detects upper digestive system disease. The method of collecting a specimen includes: a step of administering a stimulant of pancreatic juice secretion or a stimulant of bile secretion to a subject; a step of positioning sampling equipment in the duodenum of the subject into which duodenal juice is secreted, the sampling equipment being used to collect and store the duodenal juice; a step of starting collection of the duodenal juice by the sampling equipment within five minutes from the administration of the stimulant of pancreatic juice secretion or the stimulant of bile secretion; and a step of stopping collection of the duodenal juice such that collection time for the duodenal juice is within five minutes from the start of collection.

24 Claims, 9 Drawing Sheets

METHOD OF COLLECTING SPECIMEN AND METHOD OF DIAGNOSING SUBJECT TO DETECT UPPER DIGESTIVE SYSTEM DISEASE

CROSS REFERENCE TO RELATED APPLICATION

This application is based upon and claims the benefit of priority from the prior provisional U.S. patent application Ser. No. 61/471,868, filed Apr. 5, 2011, the entire content of which is incorporated herein by reference.

BACKGROUND OF THE INVENTION

1. Field of the Invention

The present invention relates to a method of collecting a specimen and a method of diagnosing a subject to detect upper digestive system disease. In particular, the present invention relates to a method of collecting a specimen and a method of diagnosing a subject suitable for detection of early cancers, such as pancreatic cancer, biliary tract cancer, and liver cancer.

2. Description of the Related Art

Rapid advancements are being made in methods of examination for upper digestive system diseases (for example, pancreatic cancer, biliary tract cancer, gallstones, stomach cancer, cholecystitis, pancreatitis, liver cancer, and cirrhosis). The prognosis is extremely poor particularly for pancreatic cancer and biliary tract cancer among the upper digestive system diseases. A method of examination is required to enable detection of early stages of these cancers.

Conventionally, research has been reported regarding an early method of examination for cancers in which pancreatic juice and bile are used as specimens. In the method of examination, cytological diagnosis and protein analysis are performed on these specimens. However, in the case of collecting the pancreatic juice or the bile, it is required to insert a catheter into the pancreatic duct or the bile duct. Doctors are required to acquire significant skill in catheter insertion. In addition, catheter insertion may cause pancreatitis as an accidental symptom. Therefore, not all doctors can easily perform the method of examination using pancreatic juice and bile.

A method of pancreatic juice collection is reported in which a catheter is not inserted into the pancreatic duct or the bile duct. Rather, duodenal juice is collected from the duodenum. The duodenal juice contains pancreatic juice and bile discharged from the pancreas and the gall bladder into the duodenum. The duodenal juice is then examined.

For example, "Clinical Gastroenterology and Hepatology 2006; 4(6) pp. 782-789" reports a method of detecting pancreatic cancer in which the interleukin-8 (IL-8) protein concentration present in duodenal juice containing pancreatic juice is measured using the enzyme-linked immunosorbent assay (ELISA) method. In this method, an upper gastrointestinal endoscope is inserted into the patient after fasting. A stimulant of pancreatic juice secretion (secretin) is then administered. Subsequently, pancreatic juice secreted from the duodenal papilla is collected from the duodenum. The pancreatic juice is collected for ten minutes using a catheter that has been threaded through the endoscope. Then, the duodenal juice is frozen for preservation. In addition, the report indicates that a protease inhibitor is added to the collected duodenal juice. It is reported that, as a result, pancreatic cancer can be detected with high sensitivity.

U.S. Pat. No. 5,651,769 reports a method of diagnosing chronic pancreatitis in which duodenal juice is collected from the duodenum using an endoscope. In this method, to prevent gastric juice from mixing with the duodenal juice, a double-lumen catheter is used to collect the duodenal juice. The double-lumen catheter is capable of collecting the gastric juice and the duodenal juice separately. In a manner similar to a secretin test conducted in the conventional method, the patient is administered secretin. Subsequently, the duodenal juice is collected for 15 minutes at a time over a one-hour period.

However, in these methods, the patient is administered a stimulant of pancreatic juice secretion (such as secretin). Therefore, the methods are invasive to patients. In addition, the cost of examination is high due to the cost of the required drugs.

In addition, the collection time for duodenal juice is very long (10 minutes or 15 minutes at a time over a one-hour period). Because a large amount of time is required for examination, the burden placed on patients and doctors is also great.

Furthermore, no reports have been made regarding the timing at which the protease inhibitor is added to the duodenal juice. Therefore, if the protease inhibitor is added to the duodenal juice after the duodenal juice has been collected for 10 minutes or 15 minutes at a time over a one-hour period, the proteins and cells to be measured are broken down by the protease activated in the duodenal juice while the duodenal juice is being collected and accumulated. Therefore, detection accuracy of proteins and cells may decrease.

SUMMARY OF THE INVENTION

The present invention has been achieved in light of the issues of the conventional method of examination described above. In particular, an object of the present invention is to simplify the method of examination and improve examination accuracy.

According to an aspect of the present invention, a method of collecting a specimen to detect upper digestive system disease is provided. The method of collecting a specimen includes: a step of administering a stimulant of pancreatic juice secretion or a stimulant of bile secretion to a subject; a step of positioning sampling equipment in the duodenum of the subject into which duodenal juice is secreted, the sampling equipment being used to collect and store the duodenal juice; a step of starting collection of the duodenal juice by the sampling equipment within five minutes from the administration of the stimulant of pancreatic juice secretion or the stimulant of bile secretion; and a step of stopping collection of the duodenal juice such that collection time for the duodenal juice is within five minutes from the start of collection.

In addition, according to another aspect of the present invention, a method of diagnosing a subject to detect upper digestive system disease is provided. The method of diagnosing a subject includes: a step of administering a stimulant of pancreatic juice secretion or a stimulant of bile secretion to a subject; a step of positioning a sampling equipment in the duodenum of the subject into which duodenal juice is secreted, the sampling equipment being used to collect and store the duodenal juice; a step of starting collection of the duodenal juice by the sampling equipment within five minutes from the administration of the stimulant of pancreatic juice secretion or the stimulant of bile secretion; a step of stopping collection of the duodenal juice such that collection time for the duodenal juice is within five minutes from the start of collection; and a step of detecting concentration of a protein included in the collected duodenal juice using an immunochromatography method; and a step of detecting concentration of a protein included in the collected duodenal juice using an immunochromatography method.

According to an aspect of the present invention, a method of collecting a specimen to detect upper digestive system disease is provided. The method of collecting a specimen includes: a step of administering a stimulant of pancreatic juice secretion or a stimulant of bile secretion to a subject; a step of positioning sampling equipment in the duodenum of the subject into which duodenal juice is secreted, the sampling equipment being used to collect and store the duodenal juice; a step of starting collection of the duodenal juice by the sampling equipment within five minutes from the administration of the stimulant of pancreatic juice secretion or the stimulant of bile secretion; and a step of stopping collection of the duodenal juice when collection quantity of the duodenal juice reaches a predetermined quantity which is 3.0 ml or less.

According to another aspect of the present invention, a method of diagnosing a subject to detect upper digestive system disease is provided. The method of diagnosing a subject includes: a step of administering a stimulant of pancreatic juice secretion or a stimulant of bile secretion to a subject; a step of positioning a sampling equipment in the duodenum of the subject into which duodenal juice is secreted, the sampling equipment being used to collect and store the duodenal juice; a step of starting collection of the duodenal juice by the sampling equipment within five minutes from the administration of the stimulant of pancreatic juice secretion or the stimulant of bile secretion; a step of stopping collection of the duodenal juice when collection quantity of the duodenal juice reaches a predetermined quantity which is 3.0 ml or less; and a step of detecting concentration of a protein included in the collected duodenal juice using an immunochromatography method.

BRIEF DESCRIPTION OF THE DRAWINGS

In the accompanying drawings:

FIG. 8A and FIG. 8B are views showing S100P concentration in the duodenal juice accompanying the elapse of time.

FIG. 9A and FIG. 9B are views showing IL-8 protein concentration in the duodenal juice every fractionation of collection.

DETAILED DESCRIPTION OF THE PREFERRED EMBODIMENTS

A method of collecting a specimen and a method of diagnosing a subject to detect upper digestive system disease of the present invention will hereinafter be described using examples, with reference to the drawings.

The upper digestive system disease that can be detected by the present invention can be any disease occurring in an organ in which fluid secreted from the organ mixes with duodenal juice. Specifically, the upper digestive system diseases include diseases occurring in the pancreas or the biliary tract. In addition, the upper digestive system diseases include diseases occurring in the liver that produces bile and diseases occurring in the stomach. Diseases occurring in the pancreas or the biliary tract include, for example, pancreatic cancer, intraductal papillary mucinous neoplasm (IPMN), mucinous cystic neoplasm (MCN), chronic pancreatitis, acute pancreatitis, bile duct cancer, gallbladder cancer, cholangitis, cholecystitis, and gallstones. Diseases occurring in the liver that produces bile include, for example, liver cancer, cirrhosis, and hepatitis. Diseases occurring in the stomach include, for example, stomach cancer, scirrhous stomach cancer, submucosal tumors, and gastric ulcer. In the examples described hereafter, pancreatic cancer and IPMN are detected.

Before procedures of the method of collecting a specimen for detecting upper digestive system disease are described, sampling equipment and an observation device will be described.

(Sampling Equipment)

The sampling equipment is inserted into the body of a subject that is a patient. The sampling equipment collects duodenal juice and stores the collected duodenal juice.

Figure 1:
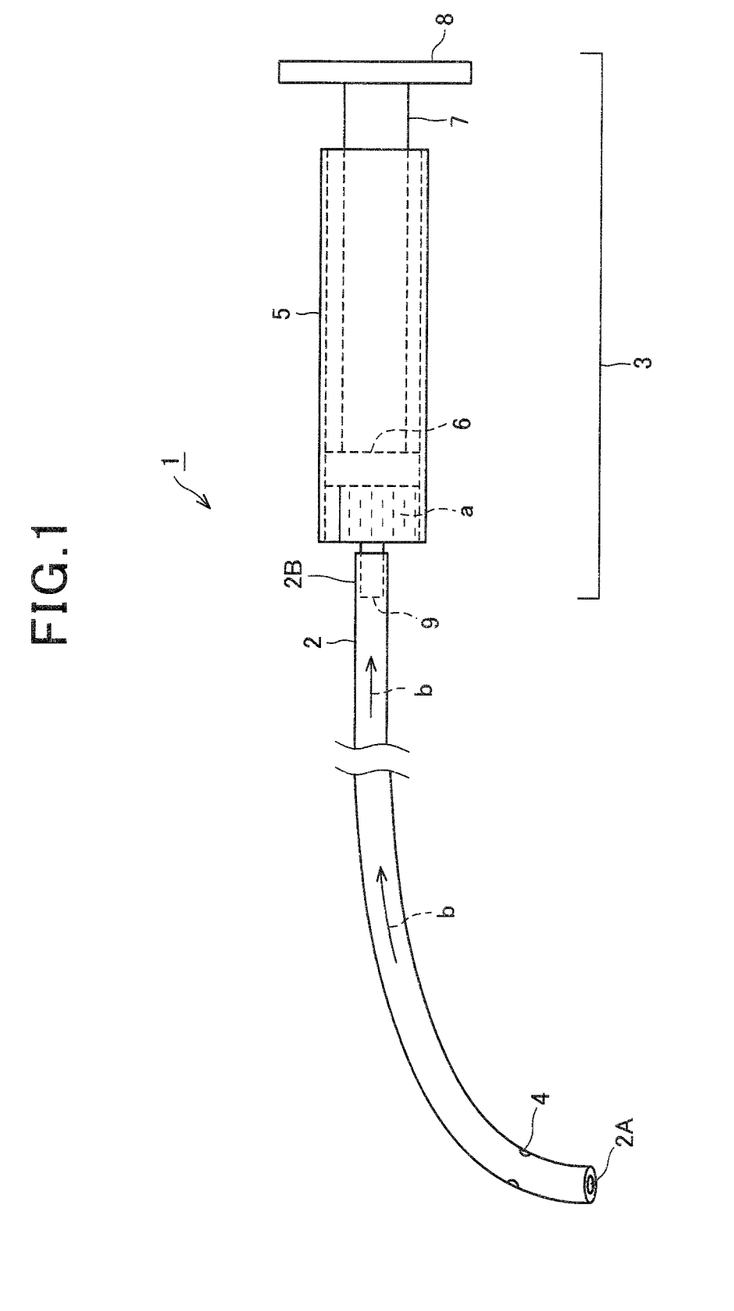
FIG. 1 is a drawing showing the constitution of the sampling equipment.

As shown in FIG. 1, the sampling equipment 1 is composed of a catheter 2 for collection and a syringe 3. The syringe 3 is a collection container capable of storing therein the duodenal juice. The syringe 3 is connected to the catheter 2. Here, a tip end section of the catheter 2 that is inserted into the subject first is referred to as a "tip 2A" or a "tip side 2A". A section on the opposite side that is operated by an operator is referred to as a "base 2B" or a "base side 2B". The longer direction of the linear shape of the catheter 2 is referred to as an "axial direction (in some instances, the longer direction)". The direction of a plane perpendicular to the axial direction is referred to as a "radial direction".

For example, an endoscopic retrograde cholangiopancreatography (ERCP) cannula PR-130Q (manufactured by Olympus Medical Systems Corporation) can be used as the catheter 2 for collection of the duodenal juice. For this collection, the cannula PR-130Q is provided with two holes 4 in the radial direction on the tip side 2A.

The syringe 3 houses a gasket 6 and a plunger 7 within a cylindrical outer casing 5. The gasket 6 is slidable in the longer direction of the outer casing 5. The plunger 7 is connected to the gasket 6. A flange 8 is connected to the plunger 7 in the end section on the side opposite to the side on which the gasket 6 is connected. The flange 8 is capable of operating the gasket 6 so as to move. A nozzle 9 is attached to the outer casing 5. The nozzle 9 is inserted into the end section on the base side 2B of the catheter 2. A protease inhibitor as a stabilizer a for duodenal juice is added in advance into a sealed space formed by the outer casing 5 and the gasket 6. The collected duodenal juice b is led through the catheter 2 into the syringe 3.

The sampling equipment 1 is not limited to the catheter 2 described in the above example. The sampling equipment 1 is merely required to be capable of being threaded through a forceps insertion opening of an endoscope and collecting duodenal juice b. Aspiration, absorption, collection, and the like can be used as the collection method. However, the collection method is not limited thereto. The collection container storing therein the duodenal juice b when the catheter 2 is used is not limited to the syringe 3. A collection trap set in front of the syringe 3 or a collection bottle connected to a vacuum pump may be used. As a result of negative pressure being generated within the catheter 2 by the collection container, the duodenal juice b can be aspirated and stored within the collection container.

(Observation Device)

The observation device is composed of an endoscope and a monitor. The endoscope is inserted into the stomach or the duodenum and inputs an image of the interior of the organ. The monitor outputs the image from the endoscope.

The catheter 2 for collection is inserted into the forceps insertion opening of the endoscope and projected outward from the tip section of the endoscope. The tip of the endoscope is positioned using the image displayed in the monitor. As a result, the position of the tip 2A of the catheter 2 can be accurately decided.

The endoscope is merely required to be a commonly used endoscope. For example, a side-view endoscope often used in the biliopancreatic region or an upper gastrointestinal endoscope used to examine the stomach and the duodenum can be used. The insertion path of the endoscope may be oral or nasal.

The procedures of the method of collecting a specimen to detect upper digestive system disease according to the present embodiment will hereinafter be described in time series with reference to FIG. 2.

Figure 2:
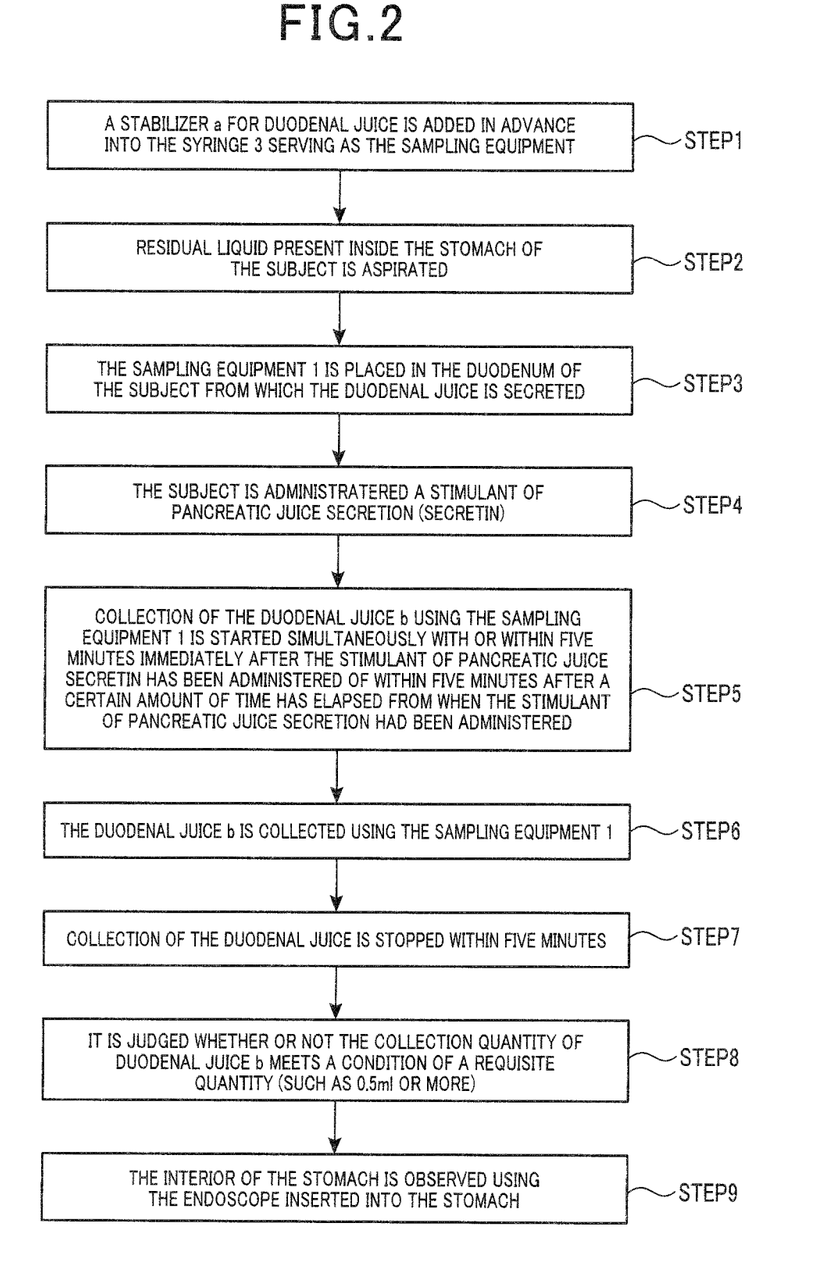
FIG. 2 is an explanatory flowchart showing procedures of the method of collecting a specimen to detect upper digestive system disease according to an embodiment of the present invention.

As shown in FIG. 2, the following steps are performed.

(1) A stabilizer a for duodenal juice b is added in advance into the syringe 3 serving as the sampling equipment 1 (Step 1).

The duodenal juice b contains a large quantity of pancreatic enzyme activated by enterokinase in the duodenum. The pancreatic enzyme rapidly degrades proteins and cells. Therefore, a protease inhibitor (such as ethylenediaminetetraacetic acid [EDTA], aprotinin, phenylmethylsulfonyl fluoride [PMSF], or 4-(2-aminoethyl) benzenesulfonyl fluoride hydrochloride [AEBSF]) or a pH-control chemical reagent that suppresses pancreatic enzyme activity is preferably enclosed in advance, as the stabilizer a for duodenal juice b, in the syringe 3 connected to the base side 2B of the catheter 2.

When collection of the duodenal juice b through the catheter 2 is started, the duodenal juice b is led into the syringe 3. Here, the stabilizer a for duodenal juice b is added into in the syringe 3 in advance. Therefore, the duodenal juice b mixes with the stabilizer a for duodenal juice b. Pancreatic enzyme activity can be instantly suppressed.

The stabilizer a for duodenal juice b may be in powder or liquid form. The stabilizer a for duodenal juice b preferably mixes quickly with the collected duodenal juice b. Depending on the type of protein, described hereafter, addition of the stabilizer a for duodenal juice b may not be required. However, for most proteins, detection accuracy is improved by the stabilizer a for duodenal juice b being added.

The protease inhibitor may be dispersed within the body. In this instance, a protease inhibitor that can be internally administered, such as Futhan or aprotinin that can injected intravenously, can be used.

(2) Residual liquid present inside the stomach of the subject is aspirated (Step 2).

The throat of the patient after fasting overnight is anesthetized. The endoscope is then inserted orally. At this time, use of a sedative agent or an antispastic agent is ordinarily preferred.

The endoscope is advanced from the esophagus to the stomach of the patient. The gastric juice that has already oozed out into the stomach is then aspirated.

Here, washing of the stomach walls by sprinkling water from the endoscope is not actively performed. Therefore, changes in the concentration to be measured (protein concentration) can be prevented. The changes in the concentration occur as a result of the gastric juice and the fluid for washing the stomach flowing into the duodenum, and mixing with the duodenal juice that is already accumulated.

(3) The sampling equipment 1 is placed in the duodenum of the subject from which the duodenal juice b is secreted (Step 3).

The endoscope is advanced to the duodenum. When confirmation is obtained visually (via camera connected to the endoscope) that the endoscope has reached the duodenum, the catheter 2 for aspiration is inserted into the forceps insertion opening of the endoscope and projected outward from the tip section of the endoscope. Preparation for collecting the duodenal juice b is made.

(4) The subject is administered a stimulant of pancreatic juice secretion (such as secretin) (Step 4).

A secretin for gastrointestinal hormones can be used as the stimulant of pancreatic juice secretion. For example, ChiRhoStim (registered trademark) manufactured by ChiRhoClin, Inc. is commonly used. The secretin is administered by intravenous injection. The pancreatic juice is secreted about one minute after administration. Therefore, the endoscope is preferably placed at the duodenum before administration of secretin. As the stimulant of bile secretion, cholecystokinin for gastrointestinal hormones can be used. The stimulant of pancreatic juice secretion and the stimulant of bile secretion are not limited to the above-described substances. The stimulant of pancreatic juice secretion and the stimulant of bile secretion are merely required to a substance providing an effect of pancreatic juice or bile secretion.

The catheter 2 may be projected from the endoscope in advance or may be projected after administration of secretin.

(5) Collection of the duodenal juice b using the sampling equipment 1 is started simultaneously with or within five minutes immediately after the stimulant of pancreatic juice secretion has been administered, or within five minutes after a certain amount of time has elapsed from when the stimulant of pancreatic juice secretion had been administered (Step 5).

The inventors of the present invention have found that, when the stimulant of pancreatic juice secretion (secretin) is administered to the subject, the concentration of proteins in the duodenal juice b decreases with the elapse of time. Specifically, when CEA that is a tumor marker is studied, the CEA concentration is found to have decreased by almost half ten minutes after administration of secretin. Therefore, when the collection timing after administration of secretin differs among patients, a difference of several seconds may be ignored. However, a difference of several minutes may lead to errors in the judgment result. Therefore, it is important that the timing at which collection is started is matched in advance for each subject. Specifically, collection may be started simultaneously with or immediately after administration of secretin. Alternatively, collection may be started one minute after administration of secretin at which time the effect of pancreatic juice secretion by secretin can be expected.

Here, the collection time for duodenal juice b is within five minutes after administration of secretin. The effect of decrease in protein concentration is considered to be small during this amount of time. However, the collection time is preferably four minutes and more preferably three minutes after administration of secretin.

When the duodenal juice b is collected after a certain amount of time has elapsed from when the stimulant of pancreatic juice secretion had been administered, the time may be clocked from immediately after administration of secretin. An alarm may ring to give notification of the collection timing when a predetermined time is reached. The duodenal juice b can thereby be collected.

(6) The duodenal juice b is collected using the sampling equipment 1 (step 6).

To detect upper digestive system disease, duodenal juice containing large quantities of pancreatic juice and bile is preferably collected. The position from which the duodenal juice b is collected will be described.

Figure 3:
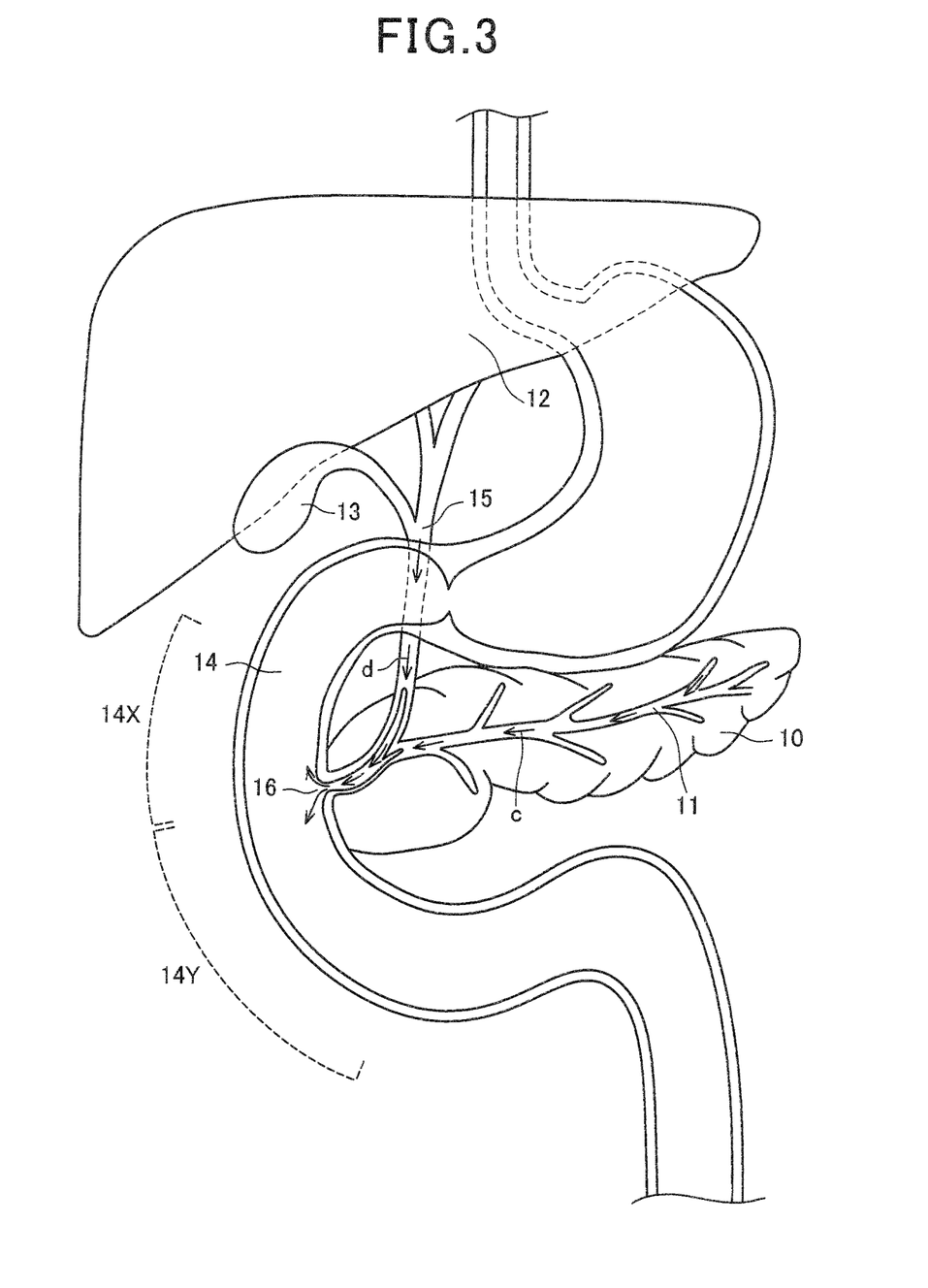
FIG. 3 is an explanatory drawing showing the position from which the duodenal juice is collected.

As shown in FIG. 3, pancreatic juice c is produced and secreted by the pancreas 10. The pancreatic juice c accumulates in the pancreatic duct 11 running through the center of the pancreas 10. Bile d is secreted from the liver 12. The bile d is stored by the gallbladder 13 positioned on the lower surface of the liver 12 and accumulates in the common bile duct 15 connecting the gallbladder 13 and the duodenum 14. The pancreatic duct 11 and the common bile duct 15 merge before the duodenum 14. The pancreatic juice c and the bile d are secreted into the duodenum 14 through the papilla of Vater 16.

Therefore, to collect the duodenal juice b, the tip 2A of the catheter 2 is preferably placed near the papilla of Vater 16 that secretes the pancreatic juice c and the bile d. The duodenal juice b is preferably collected from near the papilla of Vater 16. However, the position of the papilla of Vater 16 differs with the individual. The papilla of Vater 16 may be hidden behind a fold of mucosa or may not be visible in pictures due to anatomical position. In addition, depending on the collection site, the mixture ratio of pancreatic juice c and bile d and marker concentration may significantly differ from those of other sites. Therefore, the duodenal juice b from a plurality of sites is preferably collected from the overall second position 14X and third position 14Y of the duodenum 14 shown in FIG. 3. The duodenal juice b from the plurality of sites is continuously collected in the same collection container and mixed. Then, the collected duodenal juice b can be examined. As a result, a balanced examination of duodenal juice b present within the body can be conducted. Examination accuracy and repeatability can be ensured.

The bile d is yellow. Therefore, collection may be performed in locations where yellow fluid is visible.

(7) Collection of the duodenal juice b is stopped within five minutes (Step 7).

Each subject has their own timings at which the pancreatic juice c and the bile d are secreted into the duodenum 14. Conventionally, when collecting the duodenal juice b, the timings are considered to differ depending on each subject. Therefore, the duodenal juice b is collected over a long period of time after administration of the stimulant of pancreatic juice secretion (such as secretin). However, the inventors of the present invention have found that, when the duodenal juice b is collected over a long period of time after administration of secretin, protein concentration decreases with the elapse of time. Therefore, duodenal juice b of a small quantity considered to be scarcely affected by the decrease in protein concentration is collected over a short period of time. As a result, the inventors have found that proteins, described hereafter, can be detected in high concentrations and even a small quantity of duodenal juice b can be sufficient as the specimen.

Here, the collection quantity of duodenal juice b is preferably a quantity that can be collected without damaging the mucosa of the duodenum 14. The collection quantity is a lower limit quantity or more, the lower limit quantity being that required for detecting the concentration of a certain protein contained in the duodenal juice b or for cytological diagnosis. In addition, the collection quantity is the quantity of duodenal juice b naturally oozing into the duodenum 14, or more.

Therefore, the duodenal juice b is preferably collected within five minutes after administration of secretin. Specifically, the time elapsed from the start of collection is checked. Collection is stopped when five minutes have elapsed. Furthermore, the collection time may be decided in advance such that collection is performed for five minutes from the start of collection. On the other hand, the collection time within five minutes may be adjusted while the collection quantity of duodenal juice b is being visibly confirmed.

When the pancreatic duct 11 or the bile duct 15 of the patient is constricted by the formation of a tumor, very little pancreatic juice c may be collected even when the stimulant of pancreatic juice secretion is administered. In this instance, when collection is continued for five minutes or more, the mucosa may become damaged by excessive collection. Bleeding may occur particularly in the instance of aspiration using a catheter 2 that applies negative pressure. Therefore, collection is preferably stopped within five minutes even when the collection quantity is insufficient.

Here, a practitioner or a caretaker can monitor the collection time for duodenal juice b by measuring time simultaneously with administration of secretin or simultaneously with the start of collection of duodenal juice b using a clock, a timer, or the like. As a result of the collection time being restricting in advance in this way, the duodenal juice b can be efficiently collected in a short amount of time.

In addition, when ordinary routine upper gastrointestinal endoscopy and collection of duodenal juice b are combined, the collection time for duodenal juice b is required to be restricted. Anesthesia may wear off during observation of the gastrointestinal tract. The quantity of anesthetic to be administered becomes difficult to determine. As a result of the collection time being restricted in advance in this way, collection of the duodenal juice b and observation of the gastrointestinal tract can be simultaneously performed during the limited amount of time the patient is in the anesthetized state.

(8) It is judged whether or not the collection quantity of duodenal juice b meets a condition of a requisite quantity (such as 0.5 ml or more) (Step S8).

Specifically, the collection quantity of duodenal juice b is within a range of 0.001 ml or more and 3.0 ml or less, preferably 0.01 ml or more and 1.0 ml or less, and more preferably 0.01 ml or more and 0.5 ml or less. Specifically, the collection quantity of duodenal juice b is in a range of 0.001 ml or more and 3.0 ml or less, preferably 0.01 ml or more and 1.0 ml or less, and more preferably 0.01 ml or more and 0.5 ml or less.

The inventors of the present invention have conducted a study on numerous patients. The inventors have found that about 2.0 ml can be ordinarily collected when the duodenal juice b is aspirated for two to three minutes after administration of secretin. Although the collection quantity of duodenal juice b increases when aspiration is continued for three minutes or more, protein concentration decreases with the elapse of time and detection accuracy decreases. As a result, the collection quantity of duodenal juice b is 3.0 ml or less, preferably 1.0 ml or less, and more preferably 0.5 ml or less. The collection quantity can be restricted by the shape or function of the sampling equipment 1.

When the pancreatic duct 11 or the bile duct 15 of the patient is constricted by the formation of a tumor, very little duodenal juice b may be secreted. In this instance, if the collection quantity of the duodenal juice b is 0.001 ml, the duodenal juice b can be examined using an essentially immunological method. However, when excessive aspiration of duodenal juice b is performed on a patient in which the quantity of the specimen is clearly small, the mucosa of the duodenum 14 peels, becomes damaged, and bleeds. In some instances, the percentage of blood due to bleeding becomes greater than the percentage of duodenal juice b in the collected fluid. As a result of the collection quantity of duodenal juice b being restricted in this way, composition of the collected duodenal juice b can be kept constant. Detection accuracy can be maintained.

The collection quantity of duodenal juice b can be visibly confirmed. For example, when the catheter 2 is used, the collection quantity of the collected duodenal juice 2 is confirmed using calibrations on the syringe 3 (or the collection bottle connected to a vacuum). A calibration indicating only the requisite quantity may be displayed in advance on the collection container for duodenal juice b. Duodenal juice b that could not be completely aspirated into the container may remain in the catheter 2 during collection. Therefore, an accurate collection quantity is preferably confirmed by occasionally raising the tip section of the catheter 2 from the fluid surface, and pulling the fluid within the catheter 2 and air into the container during collection.

(9) The interior of the stomach is observed using the endoscope inserted into the stomach (Step 9).

Here, ordinary observation can be performed after the duodenal juice b is collected.

As described above, in the method of collecting a specimen according to the present embodiment, duodenal juice b of a quality and a quantity enabling examination for pancreatic disease can be collected in a short amount of time. Furthermore, duodenal juice b allowing high detection accuracy for upper digestive system disease can be collected with certainty due to administration of the stimulant of pancreatic juice secretion.

In the procedures of the method of collecting a specimen according to the present embodiment, at Step 7, it is judged whether or not the collection quantity of duodenal juice b meets the condition of the requisite quantity (such as 0.5 ml or more) set to 0.001 ml or more and 3.0 ml or less. However, this condition is not required. A procedure is possible in which only a condition for collection time is prescribed, without setting the collection quantity of duodenal juice. The condition is that collection of the duodenal juice b is stopped within five minutes from the start of collection. More preferably, collection of the duodenal juice b is stopped within two minutes. All that is required is that the requisite quantity for analysis of the specimen is collected.

[Collection System for Specimen]

An example of a collection system for a specimen will hereinafter be described. The method of collecting a specimen according to the present embodiment is implemented in the collection system.

Figure 4:
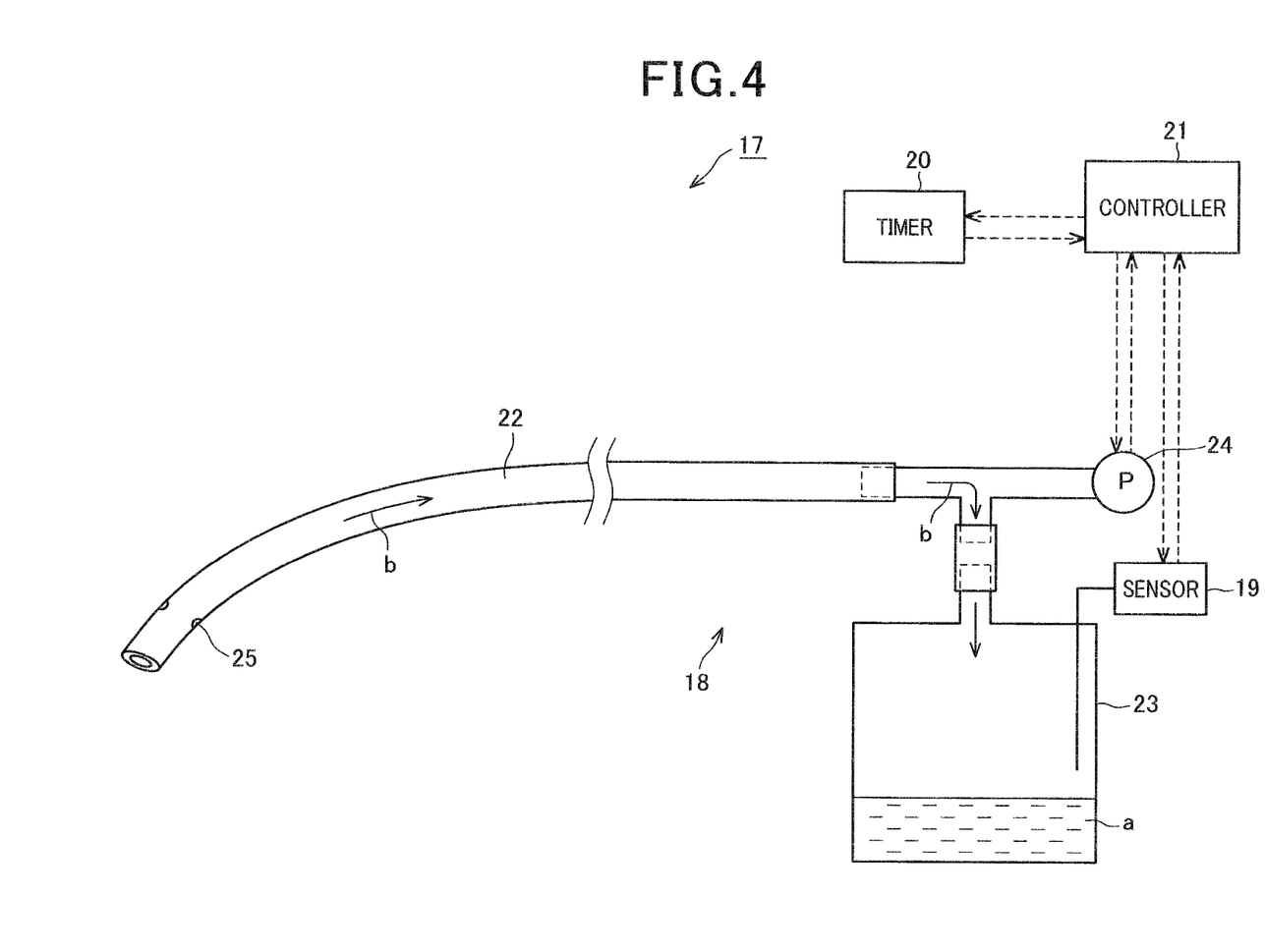
FIG. 4 is a drawing showing the constitution of a collection system for a specimen in which the method of collecting a specimen according to an embodiment of the present invention is implemented.

As shown in FIG. 4, a collection system 17 for a specimen includes sampling equipment 18, a sensor 19, and a timer 20. The sampling equipment 18 collects the duodenal juice b and stores the collected duodenal juice b. The sensor 19 detects the collection quantity of the duodenal juice b. The timer 20 detects the collection time for the duodenal juice b. The collection system 17 also includes a controller 21 and an observation device (not shown). The controller 21 controls the start and end of collection of the duodenal juice b by the sampling equipment 18 based on signals from the sensor 19 and the timer 20.

The sampling equipment 18 includes a catheter 22 for collection, a collection bottle 23, and a vacuum pump 24. The collection bottle 23 is attached to the base side of the catheter 22. The protease inhibitor is added into the collection bottle 23 in advance.

For example, the ERCP cannula PR-130Q (manufactured by Olympus Medical Systems Corporation) shown in FIG. 1 is used as the catheter 22 for collection. The ERCP cannula PR-130Q is provided with two holes 25 in the radial direction on the tip side. The sensor 19 is a fluid level detection sensor that detects the level of the duodenal juice b led into the collection bottle 23. The sensor 19 detects whether or not the collection quantity of the duodenal juice b is within a range of 0.001 ml or more and 3.0 ml or less. The sensor 19 then sends a signal to the controller 21.

The timer 20 counts five minutes from immediately after administration of the stimulant of pancreatic juice secretion (secretin) (or counts five minutes from the elapse of one minute after administration of the stimulant of pancreatic juice secretion). The timer 20 then sends a signal to the controller 21. In addition, the timer 20 counts five minutes from the start of collection of the duodenal juice b as the collection time of the duodenal juice b and sends a signal to the controller 21.

The observation device (not shown) includes an endoscope and an image monitor.

In the collection system 17 for a specimen, first, the endoscope is advanced to the duodenum 14 of the subject. Confirmation is obtained visually (via camera connected to the endoscope) using the monitor. The catheter 22 for collection is then inserted into the forceps insertion opening of the endoscope and projected outward from the tip section of the endoscope. Next, when the subject is administered the stimulant of pancreatic juice secretion (secretin), the controller 21 sends signals respectively to the vacuum pump 24, the sensor 19, and the timer 20.

When the controller 21 sends a signal to the vacuum pump 24, collection of the duodenal juice b is started as a result of startup of the vacuum pump 24. The duodenal juice b is led into the collection bottle 23. When the controller 21 sends a signal to the sensor 19, the sensor 19 detects the fluid level. When the collection quantity of the duodenal juice b meets the condition, the sensor 19 sends a signal to the controller 21. When the controller 21 sends a signal to the timer 20, the timer 20 waits five minutes from immediately after administration of the stimulant of pancreatic juice secretion or counts five minutes from the elapse of one minute after administration of the stimulant of pancreatic juice secretion. The timer 20 then sends a signal to the controller 21. When the sensor 19 or the timer 20 sends a signal to the controller 21, the controller 21 sends a stop signal to the vacuum pump 24 and stops the collection of the duodenal juice b.

In this way, the duodenal juice b is collected using a collection system 17 for a specimen in which a part of the method of collecting a specimen according to the present embodiment is automated. As a result, examination can be simplified. Moreover, the burden placed on the operator can be reduced.

[Method of Diagnosing Subject]

Next, a method of diagnosing a subject to detect upper digestive system disease according to the present embodiment will be described.

Here, measurement of protein concentration in the duodenal juice b and cytological diagnosis are performed using the duodenal juice b obtained by the above-described method of collection of a specimen shown in FIG. 2. Diagnosis of a subject is thereby performed.

(Measurement of Protein Concentration)

Any type of protein is applicable as long as the concentration thereof can be measured in the duodenal juice b and the concentration thereof changes in relation to the upper digestive system disease. Specifically, the protein may be, for example, carcinoembryonic antigen (CEA) (carbohydrate chain binding form giant tumor marker protein), S100P (calcium binding protein), or IL-8 (cytokine). When pure pancreatic juice c directly collected from the pancreatic duct 11 is examined, these proteins are known to be overexpressed in pancreatic cancer patients. The CEA, S100P, and IL-8 are proteins having different sizes, and structural and functional characteristics. However, it has become clear in the present study that these proteins are all detected in the duodenal juice b containing pancreatic juice c. In addition, correlation between the protein concentration detected from the duodenal juice b containing pancreatic juice c secreted after administration of secretin, after administration of secretin and pancreatic cancer and IPMN has also been confirmed. From these results, it is inferred that the proteins reportedly detected in the pure pancreatic juice c can be measured in the duodenal juice b collected using the method of collection of a specimen according to the present embodiment.

Furthermore, examination may be conducted using at least one protein selected from the CEA, S100P, and IL-8. Alternatively, examination may be conducted using a combination of two or more proteins. Detection accuracy can be increased by conducting examination using a combination of a plurality of proteins.

The method of measuring the concentration of protein in the duodenal juice b is merely required to be a common measuring method using antigen-antibody reaction. For example, the ELISA method, a chemiluminescence immunoassay method, a latex-coagulation method, or an immunochromatographic method may be used. In addition, as a measuring method that does not use antigen-antibody reaction, measurement can be taken by comparison of peaks and spots through time-of-flight mass spectrometry (TOF-MS) or two-dimensional electrophoresis.

In particular, the immunochromatographic method (the immunochromatography device), among the above-described methods of measuring protein, is preferably used. As a result, examination can be conducted easily and quickly in the endoscopy unit using a small quantity of duodenal juice b. In addition, the patient can be promptly informed of the result of the examination. The subsequent treatment plan can be decided on the spot.

(Immunochromatography)

The immunochromatography (the immunochromatography device) will hereinafter be described with reference to FIG. 5A and FIG. 5B.

Figure 5A:
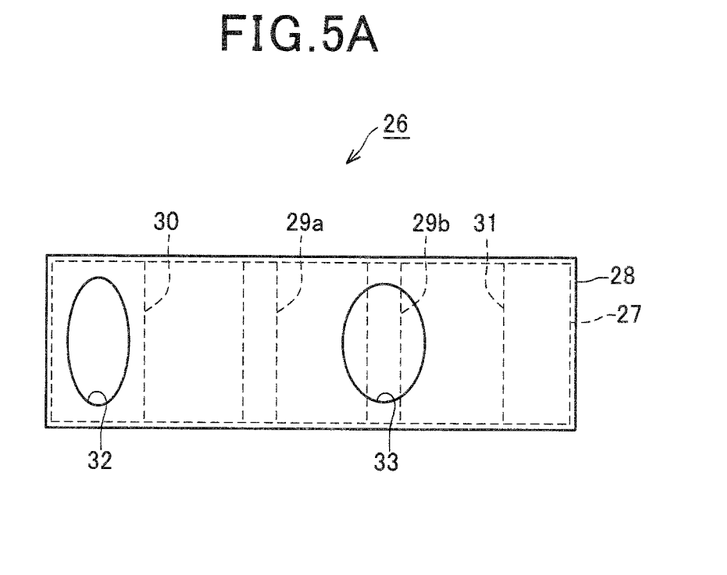
FIG. 5A is a top view showing a fundamental structure of an immunochromatography device.

As shown in FIG. 5A, an immunochromatography device 26 is basically composed of a detection unit 27 and a plastic case 28. The plastic case 28 covers the detection unit 27.

Figure 5B:
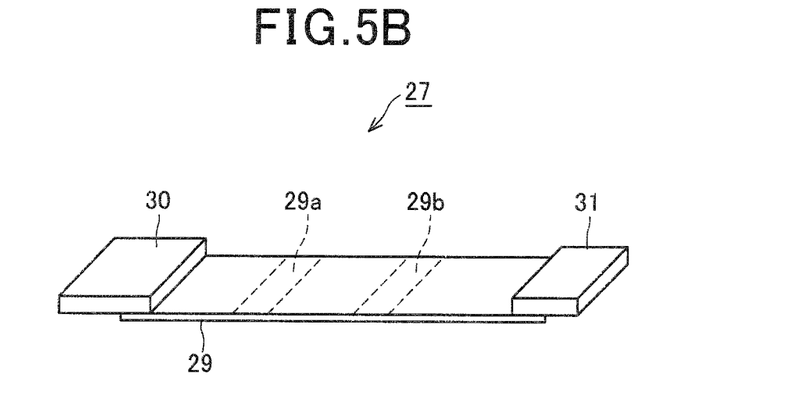
FIG. 5B is a perspective view showing a structure of detecting unit provided inside the casing of an immunochromatography device.

As shown in FIG. 5B, the detection unit 27 has a carrier 29 as a base. The subject fluid is spread over the carrier 29. A sample pad 30 is disposed on one end of the carrier 29. An absorbent pad 31 is disposed on the other end of the carrier 29. A linear first binding area 29a holding a first antibody is provided in the carrier 29. A linear second binding area 29b in which a second antibody is solid-phased is provided in a position at a distance from the first binding area 29a. As shown in FIG. 5A, a sight dome 32 is opened in a position corresponding to the sample pad 30 in the case 28. An observation window 33 is opened in a position corresponding to the second binding area 29b provided in the carrier 29.

The carrier 29 is merely required to be that on which the subject fluid can be spread. For example, a nitrocellulose membrane filter is suitable.

The first antibody of the first binding area 29a and the second antibody of the second binding area 29b are antibodies that recognize mutually differing epitopes of the protein to be detected. The first antibody is labeled by a substance having a predetermined color. The substance is, for example, a metal colloid, such as gold colloid or platinum colloid, or a latex colloid (labeled substance) such as synthetic latex or natural rubber latex. The synthetic latex is, for example, colored polystyrene latex. The labeled substance labeling the first antibody may be an enzyme or a radioactive material.

The sample pad 30 is composed of a sheet or film made of a material having excellent absorption. The material is, for example, as a porous synthetic resin, such as porous polyethylene or porous polypropylene. Alternatively, the sample pad 30 is composed of, for example, cellulose paper, such as filter paper or cotton cloth, woven fabric, or nonwoven fabric.

The absorbent pad 31 is composed of a material capable of quickly absorbing and holding liquid. The material is, for example, a cotton cloth, a filter paper, or a porous plastic nonwoven fabric such as that made of polyethylene or polypropylene.

The immunochromatography device 26, configured as described above, is used as follows. The operator first drops the subject fluid from the sight dome 32 onto the sample pad 30 (or may soak the sample pad 30 in the subject fluid). The dropped subject fluid spreads by moving over the carrier 29, from the sample pad 30 towards the absorbent pad 31. During spreading, the target protein in the subject fluid binds with the first antibody in the binding area 29a and forms a complex. Then, the complex binds with the second antibody in the second binding area 29b and is absorbed in the second binding area 29b. As a result of accumulation of the complex in the second binding area 29b, the second binding area 29b is colored a predetermined color. Therefore, the operator can measure the presence or the concentration of the target protein by whether or not a band of the predetermined color appears in the observation window 33, or the darkness of the color of the band.

Here, when the collected duodenal juice is added from the sight window 32 of the immunochromatography device 26, the result can be obtained in the observation window 33 in about 15 minutes. As a result, a special examination room or an examination device is not required. The result of the examination can be quickly obtained.

(Cytological Diagnosis)

To perform cytological diagnosis, the above-described protease inhibitor is preferably mixed with the collected duodenal juice b in advance. As a result of the protease inhibitor being added, pancreatic enzyme activation is inhibited. Dissolution of cells in the pancreatic duct 11 and the bile duct 15 can be suppressed, and cell shape can be preserved. Cytological diagnosis of the duodenal juice b is performed using a method similar to that of ordinary cytological diagnosis of pancreatic juice c and bile d. Specifically, the duodenal juice b is centrifugally separated. The precipitate cells are then placed on a slide glass and fixed with alcohol. Next, the cells are Papanicolaou-stained, and the cell shapes are observed under a microscope.

Determination in cytological diagnosis is performed in five stages: Class I (no atypical cells found); Class II (atypical cells found but no suspicion of malignancy); Class III (atypical cells found but malignancy inconclusive); Class IV (atypical cells strongly suspected of malignancy found); and Class V (atypical cells concluded to be malignant).

In pancreatic cancer, bile duct cancer, and gallbladder cancer, evidence of adenocarcinoma cells are possibly seen (Class IV to V). The cytological diagnosis can be used for definite diagnosis and screening for pancreatic cancer, bile duct cancer, and gallbladder cancer.

Example 1 to Example 5 will hereinafter be described.

Example 1

An upper gastrointestinal endoscope was inserted into 38 upper digestive system disease patients (32 pancreatic cancer patients (malignant) and 6 control group patients (benign) [2 IPMN patients, 1 pancreatic endocrine tumor (NET) patient, 1 MCN patient, 1 SCN patient, and 1 retention cyst patient]: diagnostic results based on postoperative pathological diagnostic results) after fasting overnight. Gastric juice c was aspirated from each patient. When the endoscope reached the duodenum 14, a catheter 2 for aspiration (PR-130Q manufactured by Olympus Medial Systems Corporation) was inserted into the forceps insertion opening of the endoscope and projected outward from the tip section of the endoscope. The duodenal juice b was present in a plurality of sites in the second position 14X and the third position 14Y of the duodenum 14. The duodenal juice b was collected from the tip side of the catheter 2. At this time, a 20 ml syringe 3 was connected to the base side of the catheter 2.

Subsequently, in a manner similar to the conventional methods, secretin (ChiRhoStim [registered trademark]) that is a stimulant of pancreatic juice secretion was administered. The duodenal juice b was collected immediately after administration of secretin. The syringe 3 was exchanged every 2.5 minutes. The collection quantity of duodenal juice b was checked. Subsequently, the collected duodenal juice b was immediately frozen for preservation at −80° C.

Figure 6:
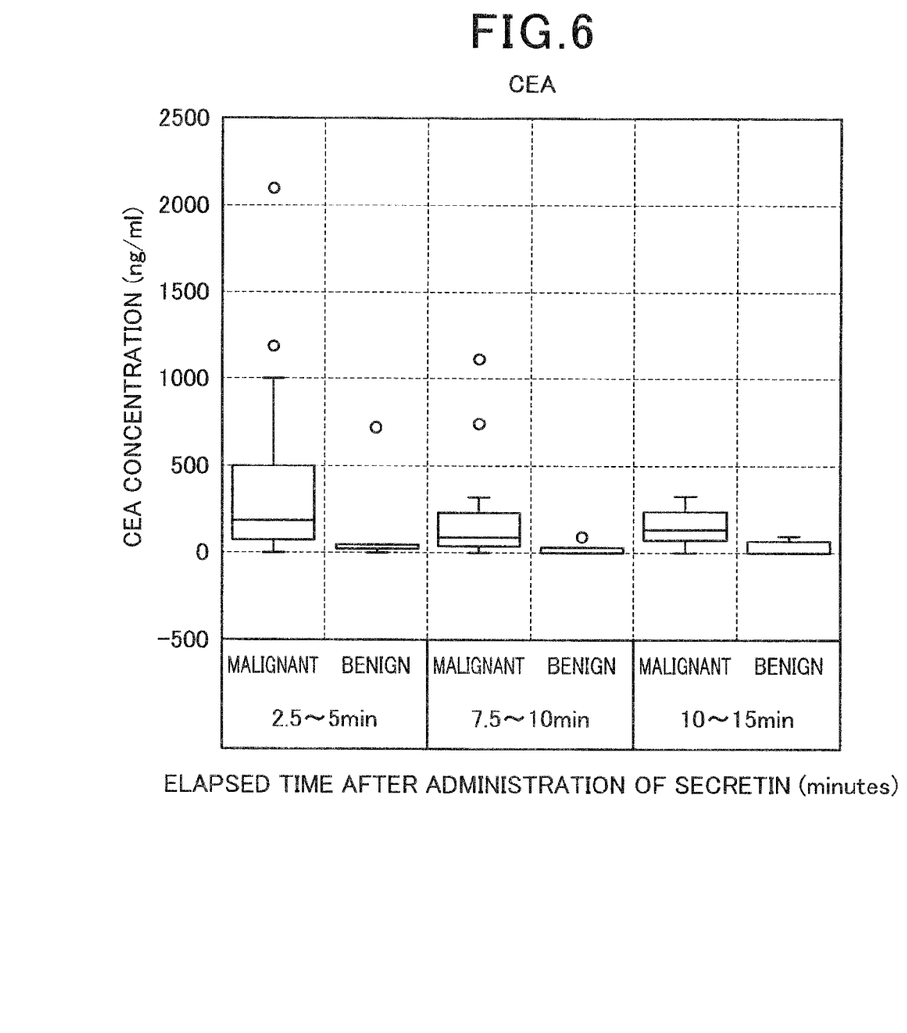
FIG. 6 is a view showing CEA concentration every fractionation of collection about duodenal juice collected in the 38 patients of pancreatic disease.

Furthermore, after the duodenal juice b had been frozen and thawed, CEA concentration in the duodenal juice b in 38 patients was measured using an ELISA kit (manufactured by IBL Co., Ltd.). The results are shown as a box-plot in FIG. 6. In FIG. 6, malignant indicates pancreatic cancer. Benign indicates the control group.

As shown in FIG. 6, it has been found that the CEA concentration in the duodenal juice b has decreased with the elapse of time after administration of secretin for almost all patients. As a result, it is indicated that variations occur in the detected protein concentration and detection accuracy decreases unless the timing at which the duodenal juice b is collected is fixed among the subjects.

In addition, the CEA concentration during the 2.5 minutes from 2.5 minutes to 5.0 minutes after administration of secretin was compared with that during the 2.5 minutes from 7.5 minutes to 10.0 minutes after administration of secretin. The CEA concentration during the 2.5 minutes from 7.5 minutes to 10.0 minutes after administration of secretin decreased by about 50% overall compared to the CEA concentration during the 2.5 minutes from 2.5 minutes to 5.0 minutes after administration of secretin.

Therefore, collecting the duodenal juice b within five minutes after administration of secretin and performing collection within a predetermined amount of time are considered preferable.

In addition, sensitivity and specificity of pancreatic cancer detection was calculated from the cut-off value calculated from the control group shown in FIG. 6. The results are shown in Table 1.

TABLE 1

| Elapsed Time From The Start Of Collection Of Duodenal Juice (minutes) | Cut-Off Value (ng/ml) | Sensitivity (%) | (n) | Specificity (%) | (n) |
| --- | --- | --- | --- | --- | --- |
| 2.5~5.0 | 49 | 84 | 26/31 | 80 | 4/5 |
| 7.5~10.0 | 21 | 84 | 28/32 | 83 | 5/6 |

As shown in Table 1, even when the duodenal juice b is continuously collected at 2.5-minute intervals, changes in the CEA concentration pattern and the sensitivity of each patient per fraction could not be seen. Therefore, it has been found that high detection accuracy can be obtained, even when the duodenal juice b is not collected continuously for 10 minutes as in the convention methods.

In measurement of the CEA concentration, no difference could be seen depending on whether or not a protease inhibitor had been added.

Furthermore, the average collection quantity of duodenal juice b accompanying the elapse of time after administration of secretin was studied.

Figure 7:
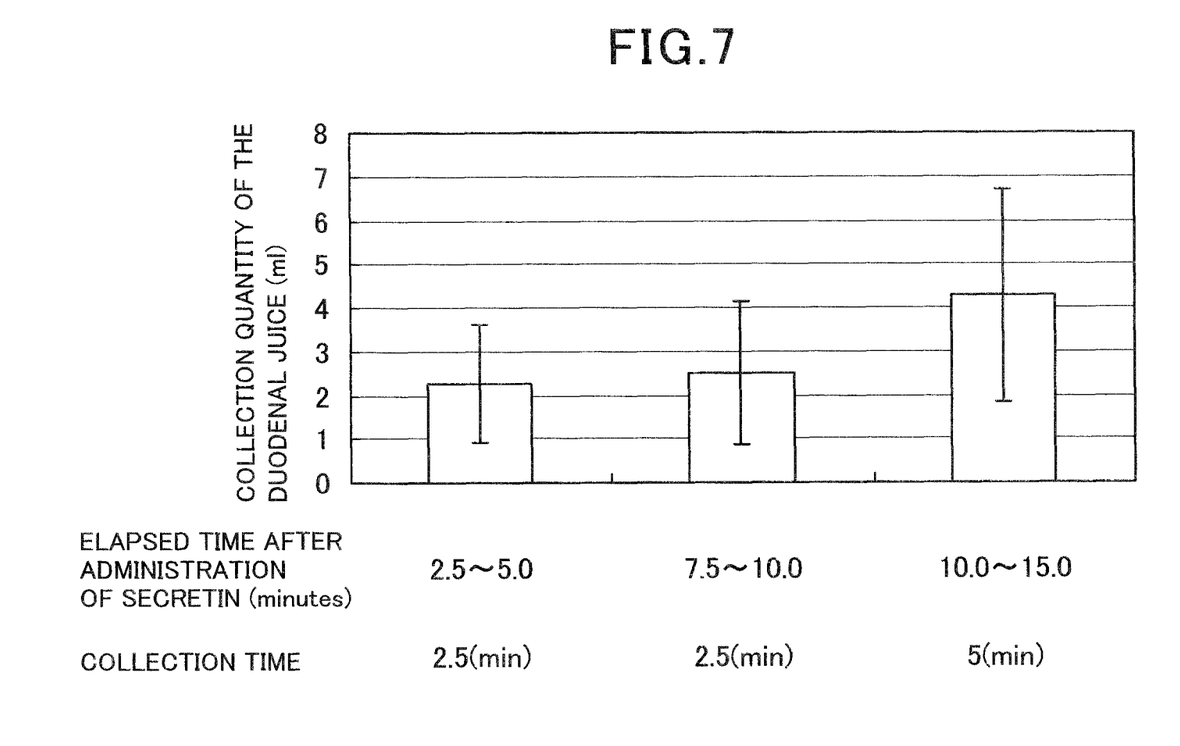
FIG. 7 is a view showing average collection quantity and dispersion for different collection times of duodenal juice collected in the 38 patients of pancreatic disease.

As shown in FIG. 7, the average collection quantity of duodenal juice b during the 2.5 minutes from 2.5 minutes to 5.0 minutes after secretin stimulation in pancreatic cancer patients was about 2.0 ml. The average collection quantity of duodenal juice b during the 2.5 minutes from 7.5 minutes to 10.0 minutes after secretin stimulation in pancreatic cancer patients was about 2.0 ml and 2.5 ml respectively. In addition, the collection quantities of duodenal juice b in pancreatic disease patients were within range of 1.0 ml to 3.5 ml. The collection quantity differs with the individual. As a result, if the duodenal juice b is collected with a target collection quantity of about 1.0 ml to 2.0 ml, the collection time is considered to be only about 1 to 2 minutes.

Example 2

In the present example, 32 cases of pancreatic disease patients (27 cases of pancreatic cancer, 5 cases in a control group [IPMN, NET, MCN, SCN, and retention cyst]) were subjected to examination. The effects of addition of a protease inhibitor were studied.

An upper gastrointestinal endoscope was inserted into the patients of the 32 cases of upper digestive system disease after fasting overnight. Gastric juice c was aspirated from the patients. When the endoscope reached the duodenum 14, a catheter 2 for collection (PR-130Q manufactured by Olympus Medial Systems Corporation) was inserted into the forceps insertion opening of the endoscope and projected outward from the tip section of the endoscope. The duodenal juice b was present in a plurality of sites in the second position 14X and the third position 14Y of the duodenum 14. The duodenal juice b was collected from the tip side of the catheter 2.

Here, the base side of the catheter 2 was bifurcated. The catheter 2 was connected to two syringes (20 ml). One syringe was added with a protease inhibitor (Complete manufactured by F. Hoffmann-La Roche Ltd.) in advance. The other syringe was not added.

The duodenal juice b was collected by aspiration for 2.5 minutes each time, after administration of secretin.

In the syringe in which the protease inhibitor had been added, when the collected duodenal juice b was led into the syringe, the protease inhibitor is degraded and mixed with the duodenal juice b.

Figure 8A:
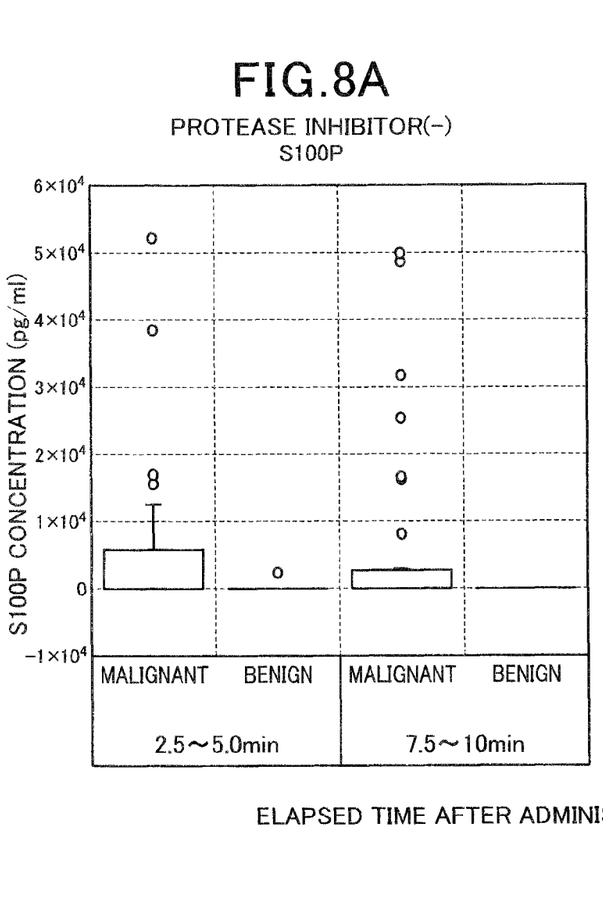
FIG. 8A is a view with no protease inhibitor added.
Figure 8B:
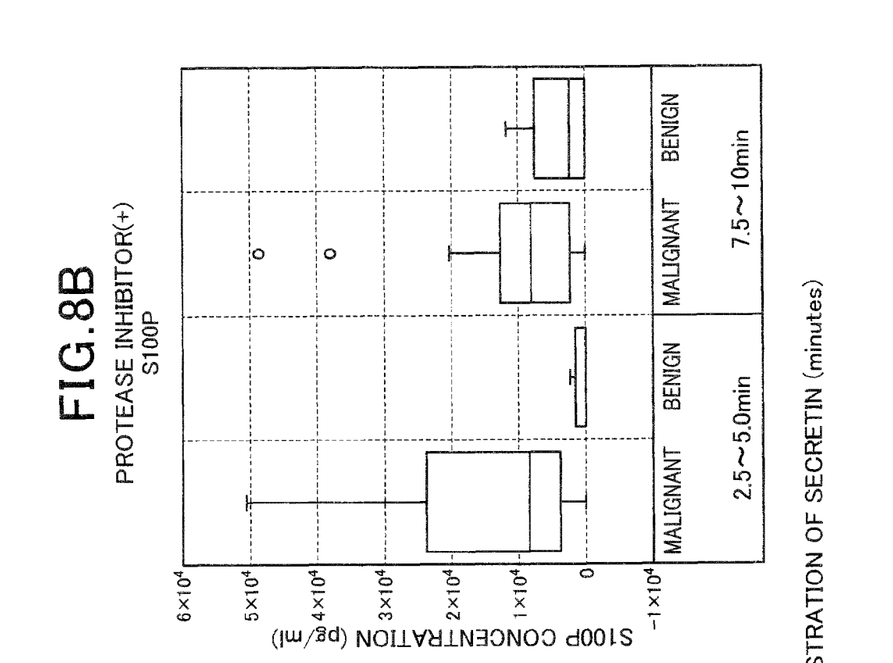
FIG. 8B is a view with protease inhibitor added.

The S100P concentration in the collected duodenal juice b was subsequently measured using the ELISA method (manufactured by Cylex Co., Ltd.). The results are shown in FIG. 8A and FIG. 8B as a box-plot. The sensitivity (%) of S100P to pancreatic cancer and IPMN is shown in Table 2. In FIG. 8A and FIG. 8B, malignant indicates pancreatic cancer. Benign indicates the control group.

TABLE 2

| Elapsed Time From The Start Of Collection Of Duodenal Juice (minutes) | Inhibitor | Cut-Off Value (pg/ml) | Sensitivity (%) | (n) | Specificity (%) | (n) |
|---|---|---|---|---|---|---|
| 2.5~5.0 | (−) | 0 | 37 | 11/30 | 80 | 4/5 |
| 7.5~10.0 |  | 0 | 42 | 13/31 | 100 | 6/6 |
| 2.5~5.0 | (+) | 1500 | 85 | 23/27 | 80 | 4/5 |
| 7.5~10.0 |  | 7384 | 50 | 13/26 | 80 | 4/5 |

As shown in FIG. 8A and FIG. 8B, it has been found that the S100P concentration in the duodenal juice b is detected to be higher when the protease inhibitor is added, compared to when the protease inhibitor is not added. In addition, as shown in Table 2, the sensitivity to pancreatic detection of the S100P is found to have significantly increased. As a result, it has been found that, when the S100P concentration in the duodenal juice b is measured, detection accuracy increases as a result of the duodenal juice b being collected with the syringe being added with a protease inhibitor in advance.

Furthermore, as shown in Table 2, when the protease inhibitor is added, the detection sensitivity to pancreatic cancer of the S100P indicates a high value of 85(%) even when the collection time for duodenal juice b is 2.5 minutes. The sensitivity from 2.5 minutes to 5.0 minutes after administration of secretin was the same as that from 7.5 minutes to 10.0 minutes after administration of secretin. As a result, the sensitivity of S100P in the duodenal juice b collected for 2.5 minutes is expected to be superior to the detection sensitivity of S100P in the duodenal juice b collected continuously for 10 minutes as in the conventional methods.

Example 3

In the present example, the IL-8 concentration in the duodenal juice b was measured using an ELISA kit (manufactured by R&D Systems Inc.). Here, the duodenal juice b was collected using the same method as that described in Example 2. The collected duodenal juice b was used as the specimen.

Figure 9A:
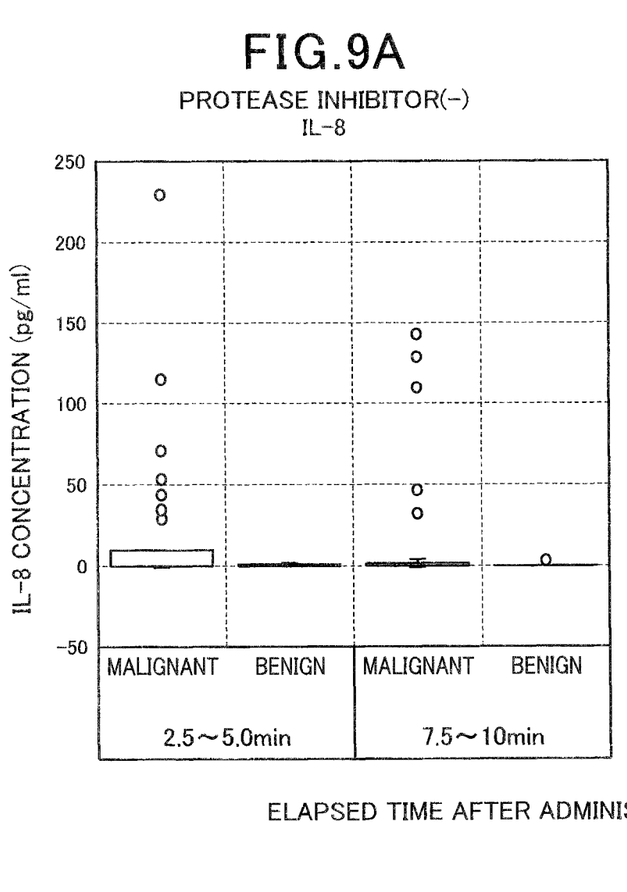
FIG. 9A is a view in the case of adding no protease inhibitor.
Figure 9B:
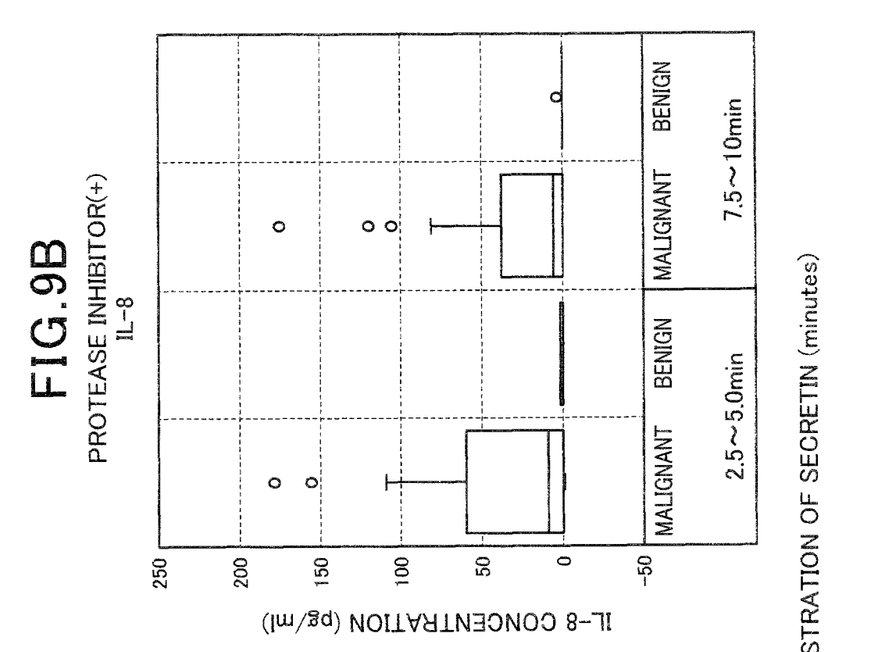
FIG. 9B is a view in the case of adding a protease inhibitor.

The results are shown in FIG. 9A and FIG. 9B as a box-plot. In FIGS. 9A and 9B, malignant indicates pancreatic cancer. Benign indicates the control group. The sensitivity (%) of IL-8 to pancreatic cancer is shown in Table 3.

TABLE 3

| Elapsed Time From The Start Of Collection Of Duodenal Juice (minutes) | Inhibitor | Cut-Off Value (pg/ml) | Sensitivity (%) | (n) | Specificity (%) | (n) |
|---|---|---|---|---|---|---|
| 2.5~5.0 | (−) | 1.5 | 37 | 11/30 | 80 | 4/5 |
| 7.5~10.0 |  | 2 | 28 | 9/32 | 83 | 5/6 |
| 2.5~5.0 | (+) | 2 | 59 | 16/27 | 100 | 5/5 |
| 7.5~10.0 |  | 1 | 62 | 16/26 | 67 | 4/6 |

As shown in FIG. 9A and FIG. 9B, it is has been found that the IL-8 concentration in the duodenal juice b significantly increases in the duodenal juice b after administration of secretin when the protease inhibitor is added, compared to when the protease inhibitor is not added. In addition, as shown in Table 3, it is has been found that the positive rate of detection to pancreatic cancer and IPMN of the IL-8 slightly increases in the duodenal juice b within five minutes after start of collection when the protease inhibitor is added, compared to when the protease inhibitor is not added.

As a result, it has been found that, when the IL-8 concentration is measured as well, detection accuracy increases as a result of the duodenal juice b being collected with the syringe being added with a protease inhibitor in advance.

Example 4

In the present example, the CEA concentration in the duodenal juice b was checked using the immunochromatography method.

Here, as an immunochromatography device, a commercially available CEA immunochromatographic examination equipment (Lana Mammo Card CEA manufactured by Nippon Kayaku Co., Ltd.) was used. As the specimen, duodenal juice b (from 2.5 minutes to 5.0 minutes after administration of secretin) collected using the same method as that in Example 1 was used.

Three microliters of the duodenal juice b secreted after administration of secretin (from 2.5 minutes to 5.0 minutes) was dropped onto the CEA immunochromatographic examination equipment. After the elapse of about 15 minutes, the CEA concentration was measured. The CEA concentration can be measured through comparison with an attached color chart.

As a result, the CEA concentration (about 100 ng/ml, and about 400 ng/ml) inferred from the color chart was correlated with the CEA concentration measured using the ELISA method. Therefore, it has been found that the CEA concentration in the duodenal juice b can be determined by the immunochromatography method.

Example 5

In the present example, cytological diagnosis of the duodenal juice b was performed.

Here, as the specimen, the duodenal juice b secreted after administration of secretin (from 2.5 minutes to 5.0 minutes) collected using the same method as that in Example 2 was used. Cytological diagnosis was performed for both when the protease inhibitor is added and when the protease inhibitor is not added.

First, the collected duodenal juice b was centrifugally separated at 700 rpm for 10 minutes using a centrifuge (manufactured by Tomy Seiko Co., Ltd.). The precipitate cells were then applied onto a slide glass and fixed with alcohol. Subsequently, the cells were Papanicolaou-stained, and the cell shapes were observed under a microscope.

As a result, the cell shapes were deformed in the fraction in which the protease inhibitor was not added. Adenocarcinoma cells could not be identified. Conversely, adenocarcinoma cells retaining cell shape could be identified in the fraction in which the protease inhibitor was added. In the pancreatic cancer patients, cells ranging from Class IV to Class V were detected.

As described above, depending on the measured component of protein concentration in the duodenal juice b, a protease inhibitor is preferably mixed with the duodenal juice b in advance. However, pancreatic disease can be detected by the duodenal juice b collected in a short amount of time at a predetermined timing after administration of secretin as in the conventional methods. The collected duodenal juice b has been found to sufficiently serve as a specimen for pancreatic cancer detection.

While there has been described what is at present considered to be these embodiments of the invention, it will be understood that various embodiments which are not described yet may be made therein, and it is intended to cover all claims within the true spirit and scope of the invention.

What is claimed is:

1. A method of collecting a specimen to detect upper digestive system disease, wherein the method includes:
    (a) positioning sampling equipment in the duodenum of a subject, into which duodenal juice is secreted, the sampling equipment being used to collect and store the duodenal juice;
    (b) administering a stimulant of pancreatic juice secretion or a stimulant of bile secretion to the subject after step (a);
    (c) starting collection of the duodenal juice by the sampling equipment within five minutes from the administration of the stimulant of pancreatic juice secretion or the stimulant of bile secretion after step (b); and
    (d) stopping collection of the duodenal juice such that collection time for the duodenal juice is within five minutes from the start of collection after step (c).

2. The method of collecting a specimen to detect upper digestive system disease according to claim 1, wherein the method includes a step of stopping collection of the duodenal juice when a collection quantity of the duodenal juice reaches a predetermined quantity which is 3.0 ml or less.

3. The method of collecting a specimen to detect upper digestive system disease according to claim 1, wherein collection of the duodenal juice by the sampling equipment is started within three minutes from the administration of the stimulant of pancreatic juice secretion or the stimulant of bile secretion.

4. The method of collecting a specimen to detect upper digestive system disease according to claim 1, wherein the upper digestive system disease is a pancreaticobiliary disease.

5. The method of collecting a specimen to detect upper digestive system disease according to claim 1, wherein an amount of time from the administration of the stimulant of pancreatic juice secretion or the stimulant of bile secretion until the start of collection of the duodenal juice is the same for a plurality of subjects.

6. The method of collecting a specimen to detect upper digestive system disease according to claim 1, wherein the method includes a step of adding a stabilizer for the duodenal juice into a collection container serving as the sampling equipment, and the sampling equipment collects the duodenal juice after the administration of the stimulant of pancreatic juice secretion or the stimulant of bile secretion, and stores the duodenal juice in the collection container.

7. The method of collecting a specimen to detect upper digestive system disease according to claim 1, wherein the method includes a step of aspirating residual liquid present within the stomach of the subject before the step of positioning the sampling equipment in the duodenum of the subject.

8. The method of collecting a specimen to detect upper digestive system disease according to claim 1, wherein the method includes a step of observing the interior of the stomach by an observation device inserted into the stomach after the duodenal juice is collected by the sampling equipment.

9. A method of diagnosing a subject to detect upper digestive system disease, wherein the method includes:
    (a) positioning sampling equipment in the duodenum of the subject, into which duodenal juice is secreted, the sampling equipment being used to collect and store the duodenal juice;
    (b) administering a stimulant of pancreatic juice secretion or a stimulant of bile secretion to the subject after step (a);
    (c) starting collection of the duodenal juice by the sampling equipment within five minutes from the administration of the stimulant of pancreatic juice secretion or the stimulant of bile secretion after step (b);
    (d) stopping collection of the duodenal juice such that collection time for the duodenal juice is within five minutes from the start of collection after step (c); and
    (e) detecting concentration of a protein included in the collected duodenal juice using an immunochromatography method after step (d).

10. The method of diagnosing a subject to detect upper digestive system disease according to claim 9, wherein
    the protein is at least one or a combination of a plurality of proteins selected from CEA, S100P, and IL-8.

11. A method of diagnosing a subject to detect upper digestive system disease, wherein the method includes:
    (a) positioning sampling equipment in the duodenum of the subject, into which duodenal juice is secreted, the sampling equipment being used to collect and store the duodenal juice;
    (b) administering a stimulant of pancreatic juice secretion or a stimulant of bile secretion to the subject after step (a);
    (c) starting collection of the duodenal juice by the sampling equipment within five minutes from the administration of the stimulant of pancreatic juice secretion or the stimulant of bile secretion after step (b);
    (d) stopping collection of the duodenal juice such that collection time for the duodenal juice is within five minutes from the start of collection after step (c); and
    (e) conducting examination for cytological diagnosis of the collected duodenal juice after step (d).

12. A method of collecting a specimen to detect upper digestive system disease, wherein the method includes:
    (a) positioning sampling equipment in the duodenum of a subject, into which duodenal juice is secreted, the sampling equipment being used to collect and store the duodenal juice;
    (b) administering a stimulant of pancreatic juice secretion or a stimulant of bile secretion to the subject after step (a);
    (c) starting collection of the duodenal juice by the sampling equipment within five minutes from the administration of the stimulant of pancreatic juice secretion or the stimulant of bile secretion after step (b); and (d) stopping collection of the duodenal juice when collection quantity of the duodenal juice reaches a predetermined quantity which is 3.0 ml or less after step (c).

13. The method of collecting a specimen to detect upper digestive system disease according to claim 12, wherein the method includes a step of adding a stabilizer for the duodenal juice in a collection container serving as the sampling equipment, and the sampling equipment collects naturally secreted duodenal juice and stores the duodenal juice in the collection container.

14. The method of collecting a specimen to detect upper digestive system disease according to claim 12, wherein the method includes a step of aspirating residual liquid present within the stomach of the subject before the step of positioning the sampling equipment in the duodenum of the subject.

15. The method of collecting a specimen to detect upper digestive system disease according to claim 12, wherein the upper digestive system disease is a pancreaticobiliary disease.

16. The method of collecting a specimen to detect upper digestive system disease according to claim 12, wherein the method includes a step of observing the interior of the stomach using an observation device inserted into the stomach after the duodenal juice is collected by the sampling equipment.

17. A method of diagnosing a subject to detect upper digestive system disease, wherein the method includes:

(a) positioning sampling equipment in the duodenum of the subject into which duodenal juice is secreted, the sampling equipment being used to collect and store the duodenal juice;

(b) administering a stimulant of pancreatic juice secretion or a stimulant of bile secretion to the subject after step (a);

(c) starting collection of the duodenal juice by the sampling equipment within five minutes from the administration of the stimulant of pancreatic juice secretion or the stimulant of bile secretion after step (b);

(d) stopping collection of the duodenal juice when collection quantity of the duodenal juice reaches a predetermined quantity which is 3.0 ml or less after step (c); and (e) detecting concentration of a protein included in the collected duodenal juice using an immunochromatography method after step (d).

18. The method of diagnosing a subject to detect upper digestive system disease according to claim 17, wherein the protein is at least one or a combination of a plurality of proteins selected from CEA, S100P, and IL-8.

19. A method of diagnosing a subject to detect upper digestive system disease, wherein the method includes:

(a) positioning sampling equipment in the duodenum of the subject into which duodenal juice is secreted, the sampling equipment being used to collect and store the duodenal juice;

(b) administering a stimulant of pancreatic juice secretion or a stimulant of bile secretion to the subject after step (a);

(c) starting collection of the duodenal juice by the sampling equipment within five minutes from the administration of the stimulant of pancreatic juice secretion or the stimulant of bile secretion after step (b);

(d) stopping collection of the duodenal juice when collection quantity of the duodenal juice reaches a predetermined quantity which is 3.0 ml or less after step (c); and (e) conducting examination for cytological diagnosis of the collected duodenal juice after step (d).

20. The method of diagnosing a subject to detect upper digestive system disease according to claim 9, wherein an amount of time from the administration of the stimulant of pancreatic juice secretion or the stimulant of bile secretion until the start of collection of the duodenal juice is the same for a plurality of subjects.

21. The method of diagnosing a subject to detect upper digestive system disease according to claim 11, wherein an amount of time from the administration of the stimulant of pancreatic juice secretion or the stimulant of bile secretion until the start of collection of the duodenal juice is the same for a plurality of subjects.

22. The method of collecting a specimen to detect upper digestive system disease according to claim 12, wherein an amount of time from the administration of the stimulant of pancreatic juice secretion or the stimulant of bile secretion until the start of collection of the duodenal juice is the same for a plurality of subjects.

23. The method of diagnosing a subject to detect upper digestive system disease according to claim 17, wherein an amount of time from the administration of the stimulant of pancreatic juice secretion or the stimulant of bile secretion until the start of collection of the duodenal juice is the same for a plurality of subjects.

24. The method of diagnosing a subject to detect upper digestive system disease according to claim 19, wherein an amount of time from the administration of the stimulant of pancreatic juice secretion or the stimulant of bile secretion until the start of collection of the duodenal juice is the same for a plurality of subjects.

* * * * *